United States Patent
Ravenscroft et al.

[19]

[11] Patent Number: 5,824,058
[45] Date of Patent: Oct. 20, 1998

[54] PROSTHESIS DELIVERY

[75] Inventors: Adrian C. Ravenscroft, Boston; George T. Roberts, Weston, both of Mass.

[73] Assignee: Boston Scientific Corporation, Watertown, Mass.

[21] Appl. No.: 897,944

[22] Filed: Jul. 21, 1997

Related U.S. Application Data

[63] Continuation of Ser. No. 550,511, Oct. 30, 1995, abandoned, which is a continuation of Ser. No. 65,238, May 20, 1993, Pat. No. 5,480,423.

[51] Int. Cl.$^6$ ............................. A61F 2/06; A61F 2/04; A61F 29/00
[52] U.S. Cl. ............................. 623/1; 623/12; 606/194; 606/195
[58] Field of Search ................................ 623/1, 11, 12; 606/194, 195, 196, 197, 198, 199; 604/104, 8, 96

[56] References Cited

U.S. PATENT DOCUMENTS

| | | | |
|---|---|---|---|
| 3,425,418 | 2/1969 | Chvapil et al. | 623/1 |
| 3,868,956 | 3/1975 | Alfidi et al. | 623/1 |
| 3,952,747 | 4/1976 | Kimmell, Jr. | 128/303 R |
| 4,164,045 | 8/1979 | Bokros et al. | 3/1.4 |
| 4,300,244 | 11/1981 | Bokros | 623/1 |
| 4,416,028 | 11/1983 | Eriksson et al. | 623/1 |
| 4,650,466 | 3/1987 | Luther | 604/95 |
| 4,655,771 | 4/1987 | Wallsten | 623/12 |
| 4,733,665 | 3/1988 | Palmaz | 128/343 |

(List continued on next page.)

FOREIGN PATENT DOCUMENTS

| | | |
|---|---|---|
| 0 183 372 | 6/1986 | European Pat. Off. |
| 0 274 846 A1 | 12/1987 | European Pat. Off. |
| 0 282 175 | 9/1988 | European Pat. Off. |
| 0 321 912 A1 | 12/1988 | European Pat. Off. |
| 0 357 003 | 3/1990 | European Pat. Off. |
| 0 418 677 A1 | 9/1990 | European Pat. Off. |
| 0 292 587 | 11/1990 | European Pat. Off. |
| 0 441 516 | 8/1991 | European Pat. Off. |
| 0 461 791 | 12/1991 | European Pat. Off. |
| 0 481 365 | 4/1992 | European Pat. Off. |
| 0 533 511 A1 | 7/1992 | European Pat. Off. |
| 24 61 370 | 7/1975 | Germany . |
| 36 40 745 | 6/1987 | Germany . |
| 1173811 | 12/1969 | United Kingdom . |
| 1183497 | 3/1970 | United Kingdom . |
| 1205743 | 9/1970 | United Kingdom . |
| 1565828 | 4/1980 | United Kingdom . |
| WO 83/03752 | 11/1983 | WIPO . |
| 0 221 570 B1 | 5/1987 | WIPO . |

OTHER PUBLICATIONS

Alvarado et al., "Evaluation of Polymer–coated Balloon–expandable Stents in Bile Ducts," *Radiology*, Mar., 1989, vol. 170, No. 3, pp. 975–978.

(List continued on next page.)

*Primary Examiner*—Debra S. Brittingham
*Attorney, Agent, or Firm*—Fish & Richardson, P.C.

[57] ABSTRACT

This invention provides smooth delivery and accurate positioning of prostheses in the body. In embodiments, systems are provided that include elongate members extending generally along the axis of a supporting catheter to a free ends. The elongate members extend through openings in the prosthesis to maintain the position of the prosthesis on the catheter. The prosthesis can be released from the catheter by relative axial motion of the catheter and the elongate members such that the free ends are removed from the openings in the prosthesis. In embodiments, the elongate members hold the distal end of a self-expanding stent at a desired axial location and in radial compaction as a restraining sheath is withdrawn. The friction between the sheath and stent puts the stent under tension, which reduces the radial force on the sheath wall, allowing smoother retraction. Proximal portions of the stent radially expand and axially shorten. The distal end, however, is maintained at the desired axial location and released from the catheter to contact the body lumen wall without substantial axial shortening.

2 Claims, 8 Drawing Sheets

U.S. PATENT DOCUMENTS

| | | | |
|---|---|---|---|
| 4,776,337 | 10/1988 | Palmaz | 128/343 |
| 4,800,882 | 1/1989 | Gianturco | 128/343 |
| 4,856,516 | 8/1989 | Hillstead | 128/343 |
| 4,875,480 | 10/1989 | Imbert | 623/12 |
| 4,878,906 | 11/1989 | Lindemann et al. | 623/1 |
| 4,913,141 | 4/1990 | Hillstead | 606/108 |
| 4,922,905 | 5/1990 | Strecker | 606/195 |
| 4,950,227 | 8/1990 | Savin et al. | 604/8 |
| 4,998,539 | 3/1991 | Delsanti | 606/194 |
| 5,019,090 | 5/1991 | Pinchuk | 606/194 |
| 5,026,377 | 6/1991 | Burton et al. | 606/108 |
| 5,035,706 | 7/1991 | Gianturco et al. | 606/198 |
| 5,061,275 | 10/1991 | Wallstén et al. | 623/1 |
| 5,071,407 | 12/1991 | Termin et al. | 604/104 |
| 5,078,720 | 1/1992 | Burton et al. | 606/108 |
| 5,092,877 | 3/1992 | Pinchuk | 623/1 |
| 5,133,732 | 7/1992 | Wiktor | 606/195 |
| 5,171,262 | 12/1992 | MacGregor | 623/1 |
| 5,192,297 | 3/1993 | Hull | 606/195 |
| 5,201,757 | 4/1993 | Heyn et al. | 606/198 |
| 5,480,423 | 1/1996 | Ravenscroft et al. | 623/1 |
| 5,607,466 | 3/1997 | Imbert et al. | 606/194 |

OTHER PUBLICATIONS

Barth, "Expandable Tantalum Wire Stent (Strecker): Experimental and Clinical Experience," *Angioscopy Endovascular Surgery and Interventional Techniques 1990, Current Practice and Future Trends,* Dec. 10–12, 1990, pp. 1–6.

Barth et al., "Flexible Tantalum Stents Implanted in Aortas and Iliac Arteries: Effects in Normal Canines," *Radiology,* Apr., 1990, vol. 175, No. 1, pp. 91–96.

Charnsangavej et al., "Stenosis of the Vena Cava: Preliminary Assessment of Treatment with Expandable Metallic Stents," *Radiology,* Nov., 1986, vol. 161, No. 2, pp. 295–298.

Geun–Kim et al., "Dilation of Synthetic Grafts and Junctional Aneurysms," *Archives of Surgery,* Nov., 1979 vol. 114, pp. 1296–1303.

Guidon et al., "Albumin Coating of a Knitted Polyester Arterial Prosthesis: An Alternative to Preclotting," *Annals of Thoracic Surgery,* Jun., 1984, vol. 37, No. 6, pp. 457–465.

Hall et al., "Velour Fabrics Applied to Medicine," *Journal of Biomedical Materials Research,* Jun., 1967, vol. 1, No. 2, pp. 179–196.

Kinley et al., "Compliance: A Continuing Problem with Vascular Grafts," *Journal of Cardiovascular Surgery,* Mar.–Apr., 1980, vol. 21, No. 2, pp. 163–170.

Koopman et al., "Degenerative changes in Dacron external velour vascular prostheses," *Journal of Cardiovascular Surgery,* Mar.–Apr., 1980, vol. 21, pp. 159–162.

Lawrence et al., "Percutaneous Endovascular Graft: Experimental Evaluation", *Radiology,* May, 1987, vol. 163, No. 2, pp. 357–360.

Lindenauer, "The Fabric Vascular Prosthesis," *Vascular Grafts,* pp. 450–460.

Matsumoto et al., "Tantalum Vascular Stents: In Vivo Evaluation with MR Imaging", *Radiology,* 1989, vol. 170, No. 3, pp. 753–755.

May et al., "Multiple Aneurysms in Dacron Velour Graft," *Archives of Surgery,* Mar., 1978, vol. 113, No. 3, pp. 320–321.

Medi–tech®, Boston Scientific Corporation, Strecker™ Stent product literature, 1990, 1991.

Microvasive®, Boston Scientific Corporation, Strecker™ Stent patent literature, 1990.

Microvasive®, Boston Scientific Corporation, Ultraflex™ Esophageal Prosthesis patent literature, 1992.

Mitchell et al., "Comprehensive Assessment of the Safety, Durability, Clinical Performance, and Healing Characteristics of a Double Velour Knitted Dacron Arterial Prosthesis," *Vascular Surgery,* pp. 197–212.

Mullins et al., "Implantation of balloon–expandable intravascular grafts by catherization in pulmonary arteries and systemic veins," *Circulation,* Jan., 1988, vol. 77, No. 1, pp. 188–199.

Palmaz et al., "Atherosclerotic Rabbit Aortas: Expandable Intralumiunal Grafting," *Radiology,* Sep., 1986, vol. 160, No. 3, pp. 723–726.

Palmaz et al., "Expandable Intraluminal Graft: A Preliminary Study," *Radiology,* Jul., 1985, vol. 156, No. 1, pp. 73–77.

Palmaz et al., "Expandable intraluminal vascular graft: A feasibility study," *Surgery,* Feb., 1986, vol. 99, No. 2, pp. 199–205.

Robicsek et al., Indium 111–labeled platelet deposition in woven and knitted Dacron bifurcated aortic grafts with the same patient as a clinical model, *Journal of Vascular Surgery,* Jun., 1987, vol. 5, pp. 833–837.

Rösch et al., "Experimental Intrahepatic Portacaval Anastomosis: Use of Expandable Gianturco Stents", *Radiology,* Feb. 1987, vol. 162, No. 2, pp. 481–485.

Rosseau et al., "Self–expanding Endovascular Prosthesis: An Experimental Study," *Radiology,* Sep., 1987, vol. 164, No. 3, pp. 709–714.

Sauvage et al., "Future Directions in the Develoment of Arterial Prostheses for Small and Medium Caliber Arteries," *Surgical Clinics of North America,* Feb., 1974, vol. 54, No. 1, pp. 213–228.

Schaer et al., "Treatment of malignant esophageal obstruction with silicone–coated metallic self–expanding stents", *Gastrointestinal Endoscopy,* 1992, vol. 38, No. 1, pp. 7–11.

Schatz et al., "Balloon–expandable intracoronary stents in the adult dog," *Circulation,* Aug., 1987, vol. 76, No. 2, pp. 450–457.

Sigwart et al., "Intravascular Stents to Prevent Occlusion and Restenosis After Transluminal Angioplasty", *The New England Journal of Medicine,* Mar. 19, 1987, vol. 316, No. 12, pp. 701–706.

Strecker et al., "A New Vascular Baloon–expandable Prosthesis—Experimental Studies and First Clinical Results," *Journal of Interventional Radiology,* 1988, pp. 59–62.

Strecker et al., "Expandable Tubular Stents for Treatment of Arterial Occlusive Diseases: Experimental and Clinical Results," *Radiology,* Apr., 1990, vol. 175, No. 1, pp. 97–102.

Strecker et al., "Experimentalle Untersuchungen mit einer neuen perkutan einführbaren und aufdehnbaren Gefäßendoprothese," *Fortschr. Röntgenstr.,* vol. 1987, pp. 669–672.

Strecker et al., "Perkutan implantierbare, durch Ballon aufdehnbare Gefäßprothese," *DMW,* 1988, vol. 113, pp. 538–542.

Wesolowski et al., "The compound prosthetic vascular graft: A pathologic survey," *Surgery,* Jan., 1963, vol. 53, No. 1, pp. 19–44.

Zollikofer et al., "Endovascular Stenting of Veins and Grafts: Preliminary Clinical Experience," *Radiology,* Jun., 1988, pp. 707–712.

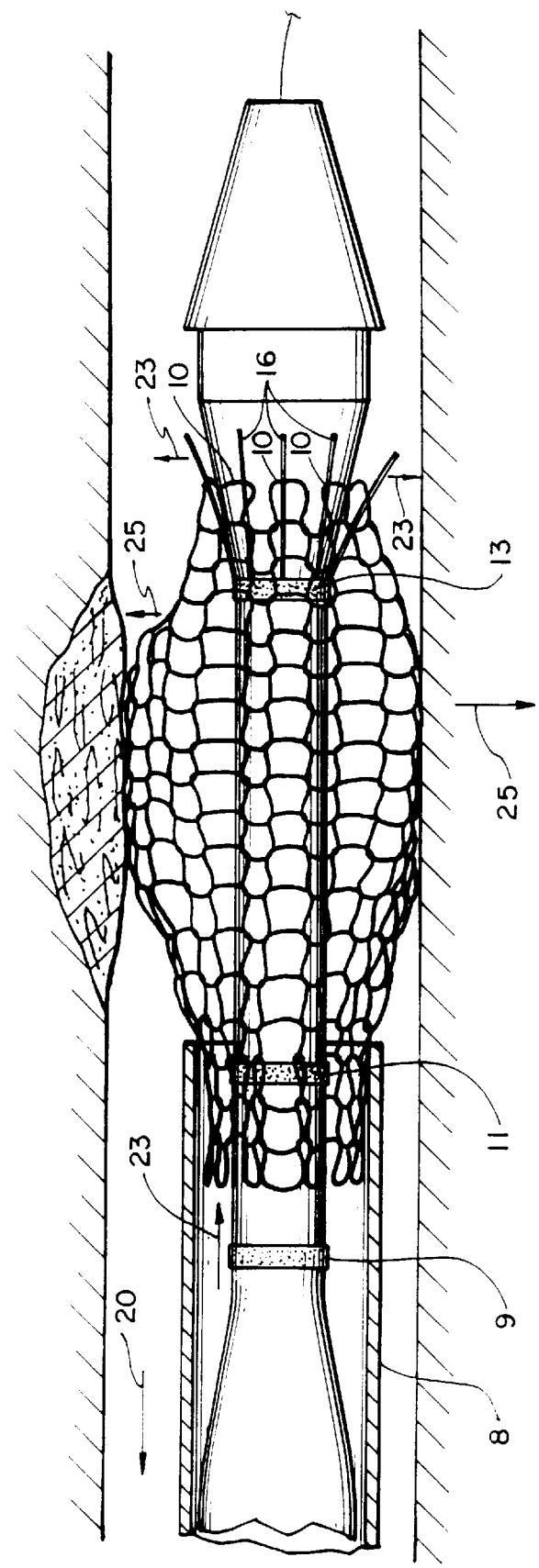

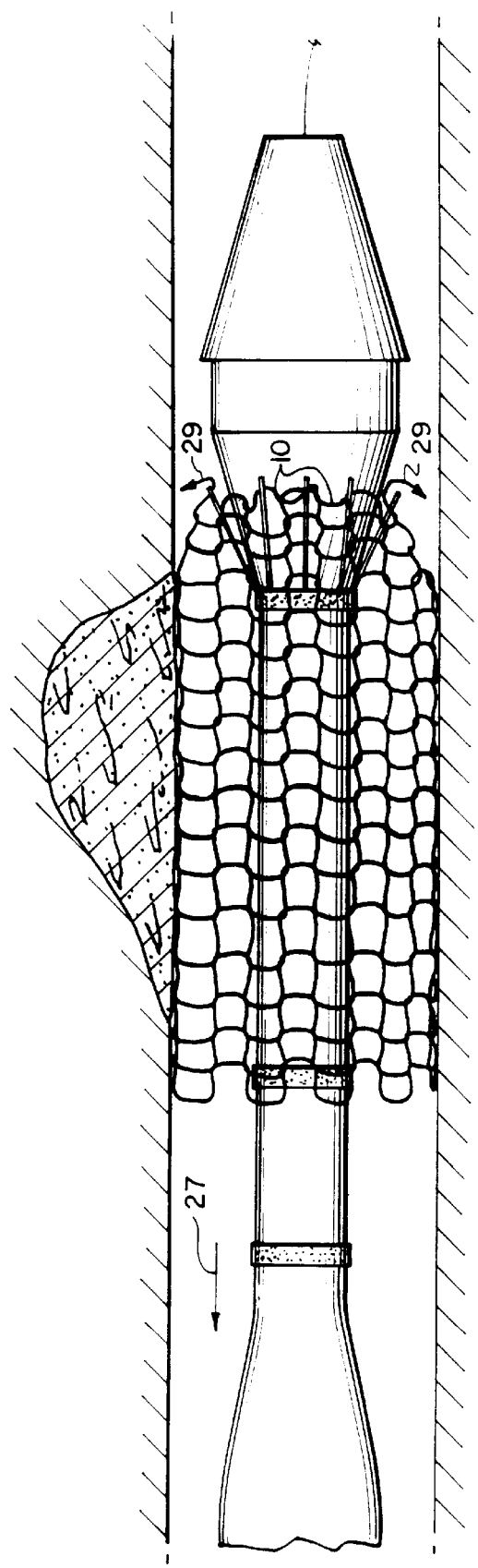

PROSTHESIS DELIVERY

This is a continuation of application Ser. No. 08/550,511, filed Oct. 30, 1995 now abandoned, which in turn is a continuation of application Ser. No. 08/065,238, filed May 20,1993, now U.S. Pat. No. 5,480,423.

FIELD OF THE INVENTION

This invention relates to delivering prostheses into the body.

BACKGROUND OF THE INVENTION

Prostheses, such as stents, grafts and the like, are placed within the body to improve the function of a body lumen. For example, stents with substantial elasticity can be used to exert a radial force on a constricted portion of a lumen wall to open a lumen to near normal size.

These stents can be delivered into the lumen using a system which includes a catheter, with the stent supported near its distal end, and a sheath, positioned coaxially about the catheter and over the stent.

Once the stent is located at the constricted portion of the lumen, the sheath is removed to expose the stent, which is expanded so it contacts the lumen wall. The catheter is subsequently removed from the body by pulling it in the proximal direction, through the larger lumen diameter created by the expanded prosthesis, which is left in the body.

SUMMARY OF THE INVENTION

This invention provides smooth delivery and accurate positioning of prostheses in the body. In embodiments, systems are provided that include elongate members extending generally along the axis of a supporting catheter to a free ends. The elongate members extend through openings in the prosthesis to maintain the position of the prosthesis on the catheter. The prosthesis can be released from the catheter by relative axial motion of the catheter and the elongate members such that the free ends are removed from the openings in the prosthesis. In embodiments, the elongate members hold the distal end of a self-expanding stent at a desired axial location and in radial compaction as a restraining sheath is withdrawn. The friction between the sheath and stent puts the stent under tension, which reduces the radial force on the sheath wall, allowing smoother retraction. Proximal portions of the stent radially expand and axially shorten. The distal end, however, is maintained at the desired axial location and released from the catheter to contact the body lumen wall without substantial axial shortening.

In an aspect, the invention features a system for positioning a prosthesis in contact with tissue within a patient. The system includes a prosthesis having proximal and distal ends and a tissue-engaging body therebetween. The prosthesis has a radially compact form for delivery into the patient and is radially expandable along its body for engaging tissue. The length of the prosthesis varies in dependence on the expansion of the body. The system further includes a catheter having a portion for supporting the prosthesis in the compact form during delivery into the patient and constructed for expanding the prosthesis in contact with tissue. The portion includes a member positioned to engage the prosthesis near the distal end to maintain a corresponding portion of the prosthesis radially compact at a predetermined axial location, while proximal portions of the prosthesis are radially expanded to engage tissue. The portion of the prosthesis engaged by the member is releasable from the catheter at an axial location substantially corresponding to the predetermined location by relative axial motion between the member and the prosthesis, so the free end of the member disengages the prosthesis.

Embodiments may include one or more of the following features. The prosthesis has, near its distal end, an opening through the tissue-engaging body and the member extends generally along the axis of the catheter to a free end that engages the prostheses by extending through the opening and the portion of the prosthesis corresponding to the opening is released by axial motion so the free end of the member is removed from the opening. The opening may include a series of openings positioned around the circumference of the prosthesis and the member is a corresponding series of elongated members, which pass through the series of openings. The member extends distally to the free end so release of the prosthesis from the catheter is by moving the members proximally relative to the prosthesis. The member is fixed on the catheter so release of the prosthesis from the catheter is by moving the catheter relative to the prosthesis. The elongate member extends at an angle with respect to the axis of the catheter to form a predefined wedge space between the member and the catheter for engaging the prosthesis. The angle is about 3–8 degrees. The member is formed of a flexible material that deflects outwardly in response to a radial force, to release the free end of the member from the opening. The member is a superelastic wire. The length of the portion of the member passing through the opening is smaller than the expanded diameter of the prosthesis. The prosthesis is a tubular-form prosthesis positioned coaxially about the supporting portion of the catheter in the radially compact form. The prosthesis is formed of a patterned filament and the opening is formed by the pattern. The prosthesis is knitted and the opening is formed by knit-loops in the knit pattern. The opening is the end loop of the knit pattern. The prosthesis is self-expanding. Portions of the self-expanding prosthesis corresponding to the member are maintained in compact form by the member and portions remote from the member are maintained in compact form by a restraint. The restraint is an axially retractable sheath and the self-expanding prosthesis engages the sheath with substantial friction to place the prosthesis under tension as the sheath is retracted.

In another aspect, the invention features a system for positioning a prosthesis in contact with tissue on the wall of a lumen of a patient. The system includes a tubular prosthesis having a proximal and distal end and a tissue-engaging body therebetween. The prosthesis has a radially compact form for delivery into the patient and is radially expandable along its body for engaging tissue. The length of the prosthesis varies in dependence on expansion of the body. The prosthesis is formed of a patterned filament and includes a series of openings through the tissue-engaging body of the prosthesis about the circumference of the prosthesis, near the distal end. The system further includes a catheter having a portion for supporting the prosthesis coaxially about the portion in the compact form for delivery into the patient and constructed for expanding the prosthesis into contact with tissue. The portion includes a series of elongate members arranged about the circumference of the catheter, fixed to the catheter, and extending generally along the axis of the catheter to free ends positioned to pass through corresponding openings about the circumference of the tissue-engaging body of the prosthesis. The members maintain corresponding portions of the prosthesis radially compact at a predetermined axial location, while proximal portions of the prosthesis are radially expanded to engage tissue. The portion of the prosthesis corresponding to the openings is releasable from the catheter at an axial location substantially corresponding to the predetermined location by moving the catheter proximally so the free ends of the members are removed from the openings.

Embodiments may include one or more of the following features. The prosthesis is self-expanding and the elongate members in the openings maintain the distal end of the prosthesis compact after other portions of the prosthesis are radially expanded. The portions of the prosthesis proximal of the members are maintained compact by a retractable sheath. The prosthesis engages the sheath with substantial friction to place the prosthesis under tension as the sheath is retracted. The elongate members are formed of superelastic metal wires. The elongate members are formed of a flexible material that deflects outwardly in response to a radial force of expansion of the prosthesis to release the free ends of the members from the openings. The length of the portions of the elongated strands passing through the loops is smaller than the expanded diameter of the prosthesis. The elongated strands extend at an angle with respect to the axis of the catheter. The angle is about 3–8 degrees.

In another aspect, the invention features a system for positioning a self-expanding prosthesis in the body. The system includes a self-expanding prosthesis having a proximal end and a distal end and a tissue-engaging body therebetween. A catheter is provided having a portion supporting a prosthesis in a radially compact form. The portion of the catheter supporting the prosthesis includes a member positioned to engage the distal end of the prosthesis to maintain corresponding portions of the prosthesis compact at a predetermined axial location with respect to the catheter while other portions of the prosthesis are radially expanded to engage tissue. The system includes a retractable sheath positioned over and in contact with the prosthesis when the prosthesis is in the compact form. A tensioning element applies an axial force to the prosthesis to reduce frictional force between the sheath and the prosthesis while retracting the sheath to expose the prosthesis.

The sheath may be a restraining sheath that maintains portions of the prosthesis compact against the radial expansion force of the prosthesis and the tensioning element is formed by the sheath, engaged by the prosthesis with substantial frictional force to place the prosthesis under tension as the sheath is retracted.

In another aspect, the invention features methods of positioning a prosthesis in the body. For example, the method may include providing a system as described above, positioning the system in a body lumen with the distal end of the prosthesis in the compact form located substantially adjacent the axial location of the lumen wall corresponding to the desired distal extension of the prosthesis, expanding portions of the prosthesis proximal of the distal end to engage the wall of the lumen, and withdrawing the catheter proximally so the distal end is disengaged from the catheter and expanded against the lumen wall. The prosthesis may be positioned at a location adjacent a side duct branching from the lumen. The body lumen may be the bile duct. Many methods are evident from the description herein.

The advantages of the invention are numerous. For example, systems of the invention can provide accurate positioning of a prosthesis, even a self-expanding stent which changes its axial length upon expansion. Accurate positioning of the prosthesis is particularly important in cases where the portion of the body lumen to be treated is adjacent a tissue feature, such as another body lumen, that should not be occluded by the prosthesis. A tumor in the bile duct that is located adjacent the duodenum is one example. It is desirable to center the prosthesis about the tumor, but care must be taken so that the end of the prosthesis does not extend beyond the duodenum. Otherwise the motion of the body and the flow of food particles may drag the stent from the bile duct.

Further features and advantages follow.

DESCRIPTION OF THE PREFERRED EMBODIMENTS

Structure

Figure 1:
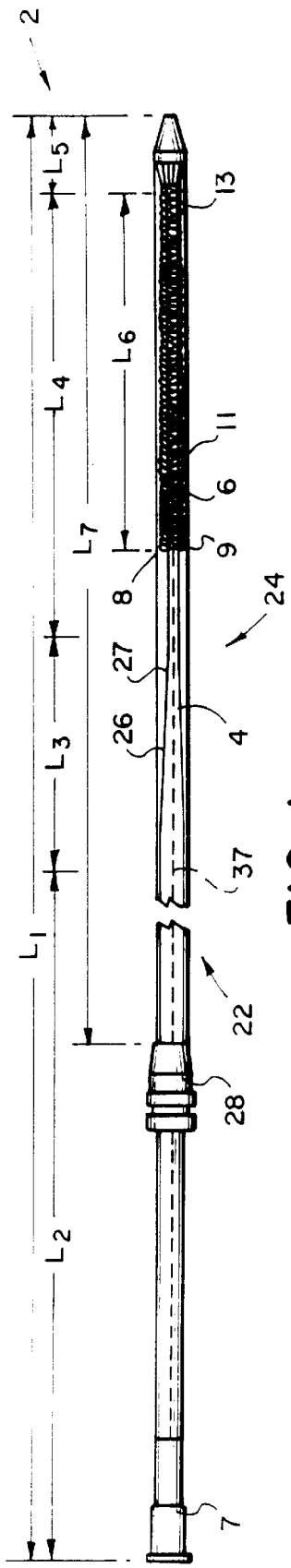
FIG. 1 is a side view, with a sheath in cross section, of a delivery system according to the invention.
Figure 1A:
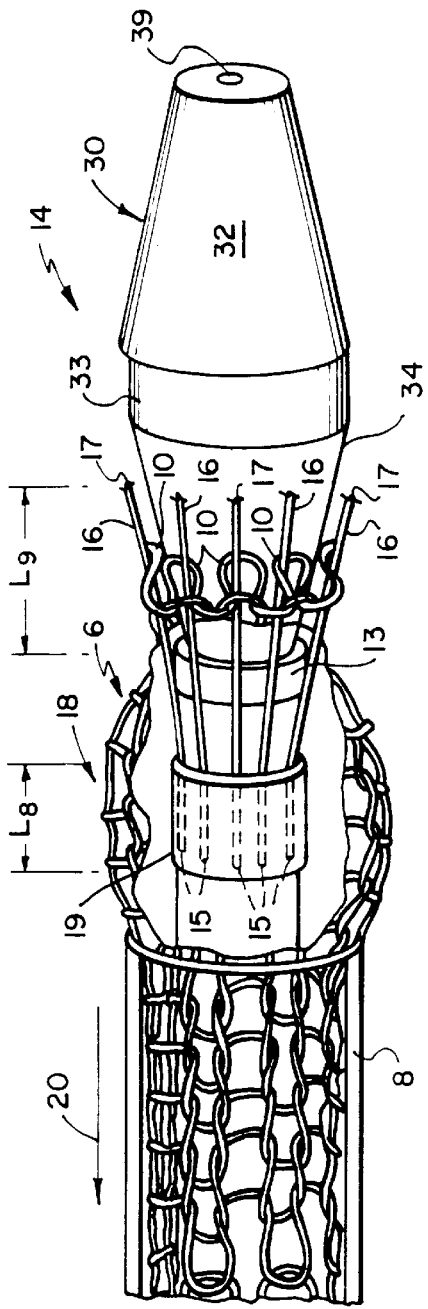
FIG. 1a is an enlarged perspective view, with the prosthesis partially cut-away, of the distal end of the system in FIG. 1 with the sheath partially retracted.

Referring to FIGS. 1–1a, a system 2 according to the invention for delivering a prosthesis to the bile duct includes a catheter body 4 carrying a prosthesis 6, which is held in a compact state for most of its length by a retractable restraining sheath 8. The prosthesis 6 is a self-expanding knit-form stent having a series of end loops 10. The distal end 14 of the catheter includes a series of flexible elongate members 16 running generally parallel to the axis of the catheter. One end of the members 16 is attached to the catheter body 4. The other, free end 17, of the members 16 extends through the end loops 10, holding the end loops at a predetermined axial position and in compact form, even when proximal portions 18 of the stent 6 expand outwardly after retraction (arrow 20) of the sheath 8. As will be discussed in further detail below, end loops 10 of the prosthesis 6 can be released from the catheter, and expanded against the lumen wall at a predetermined location, after most of the length of the stent has expanded to engage the lumen, by axially withdrawing the catheter body 4 so the free ends 17 of the members 16 slip back through the end loops 10. In this manner, the end loops 10 are positioned at a defined location along the lumen wall, even though the self-expanding stent reduces its axial length upon radial expansion due to elastic rebounding effects and the loose knit nature of the structure. Moreover, sheath retraction is smoother since the stent is placed in tension by retraction of the sheath, which simultaneously reduces the axial force on the sheath wall.

The device 2 has an overall length $L_1$, about 80 cm. The catheter body 4 (nylon) has a proximal portion 22 of constant diameter, about 0.11 inch, over a length, $L_2$, of about 69 cm, and a distal portion 24, which includes a taper 26 to a smaller diameter, about 0.053 inch, over a length, $L_3$, about 1.0 cm. Following the taper 26, a constant diameter portion 27 extends for a length, $L_4$, about 10 cm, along which the stent 6 is positioned. The catheter body 4 further includes enlarged tip 30 (nylon with radiopaque filler) of length, $L_5$, about 22 mm, maximum outer diameter 0.031 inch, with distal taper 32 (8–9 mm in length) for atraumatic advance, a step portion 33 (4 mm in length), which engages the sheath when the sheath is fully distally extended during entry into the body, and a proximal taper 34 (8–9 mm in length). A guidewire lumen 37 (phantom, FIG. 1), about 0.039 inch, for delivering the device over a guidewire, extends the length of the catheter body 4, terminating distally at an end opening 39 in the enlarged tip 30 (FIG. 1a).

The most proximal end of the body includes a luer lock device 7. The catheter includes three radiopaque markers (tantalum bands). A proximal marker 9 indicates the proximal end of the stent in the compacted state. A central marker 11 indicates the proximal end of the stent in the expanded state. A distal marker 11 indicates the distal end of the stent. As will be discussed below, the distal marker 13 also deflects wires that form members 16 off the catheter body axis.

The stent is a self-expanding knitted stent, knitted of an elastic wire material (0.005 inch diameter), such as a superelastic nitinol-type material (e.g. Strecker stent®, Boston Scientific, Watertown, Mass.). The stent includes 40 rows along its length, with 8 knit loops in each row around the circumference. In the compact condition (FIG. 1), the outer diameter of the stent is about 2.8 mm, and the length, $L_6$, about 10 cm. At full expansion, the stent has an outer diameter of 10 mm and shortens axially, to a length of about 6 cm. A feature of this invention is that the stent can be accurately positioned in spite of the axial length reduction on expansion, by maintaining the axial position of the distal end of the stent in the compact state, with members 16, while allowing the proximal portions to radially expand and axially relax. After the variations at the proximal portions, the distal end is released from the members so it expands without substantial axial variation, and contacts the lumen wall at a predetermined location determined by axially aligning the radiopaque marker 13.

The restraining sheath 8 (teflon), has a length, $L_7$, about 60 cm and a wall thickness of about 0.006 inch. A handle 28, located on portions of the sheath outside the body, is slid axially proximally to retract the sheath and expose the stent. As illustrated particularly in FIG. 1a, the stent 6 engages the inner wall of the sheath 8, owing to the elastic nature of the stent which causes it to push radially outward when in the compact state. A feature of the invention is that the sheath retraction is made easier and smoother. With only the distal end of the stent held axially in place by the members 16, the friction between the inner wall of the sheath and the stent places the stent under tension during sheath retraction, which causes the stent to elastically elongate slightly. This tension reduces the radial force of the stent on the inner wall and also prevents the loops in adjacent knit rows from intertangling and bulging radially outwardly.

The members 16 are positioned equidistantly radially about the catheter 4, with one member for each of the eight end loops of the stent. (Only five members are visible in FIG. 1a, the other three members being positioned on the opposite side of the catheter.) The members 16 are formed of straight wires (0.006 inch diameter) with an overall length of 13 mm. A proximal portion 15, length, $L_8$, about 4 mm, is attached to the catheter by a layer 19 of UV epoxy. (Another radiopaque band may cover the wires in the region between the epoxy and marker 13 and heat shrink tube may be used to cover the whole attachment assembly from epoxy 19 to marker 13.) The portion of the catheter body distal of the epoxy includes radiopaque marker 13, a tantalum band (about 0.060 inch wide) (Nobel Met, Inc., Roanoke, Va.), that creates a slight (0.003 inch) radial step from the catheter body, causing the normally straight wires to be deflected at an angle of about 3–8 degrees when the sheath is retracted. (With the sheath positioned over the wires, the free ends of the wires engage the inner wall of the sheath and the wires are bent inward slightly and partially supported against the proximal taper 34 of the enlarged end 30.) The deflected portion of the wires extend beyond the marker 13 for a distance along the catheter axis, $L_9$, about 6 mm to the free ends 17. The deflection of the wires and the taper 34 of enlarged end 30, create a predetermined space just distal of the marker 13, slightly smaller in width than the diameter of the stent wire, where the end loops are positioned. As illustrated particularly in FIG. 1a, the end loops are wedged in this space between the members 16 and taper 34. In this position the end loops are maintained axially and radially stable when the sheath is retracted, but are also easily dislodgeable from the wedged position when the catheter body is moved proximally, after proximal portions of the stent have been expanded to engage the lumen wall. The angle of the members is about equal to the angle of the taper 34 (e.g. about 8°). (The angle of the members may be made larger than the angle of the back taper 34 so friction between the end loops and back taper is reduced as the catheter is withdrawn proximally.) In this embodiment, the end loops are wedged at a location toward the proximal end of the members 16, about 1 mm from the radiopaque marker 13. In this position, the radial expansion force of the stent does not overcome the stiffness of the wires and cause them to deflect outward and prematurely release the stent. When the catheter is slid proximally, the end loops are easily dislodged from the wedged location and slide along the members until the radial force overcomes the stiffness of the members, causing them to deflect outward, and the end loops are released. The length of the members is kept smaller than the expanded radius of the stent, yet long enough to hold the end loops compact. Further, the members are formed of an elastic material, such as a superelastic nitinol-type material, that does not plastically deform when the members deflect as the prosthesis is released or as the device is being delivered along a torturous path into a duct. Other embodiments can use filaments formed of other materials, for example, stiff polymers. Embodiments may also use filaments that have high stiffness and do not deflect under the radial expansion of the stent at any positioning of the end loops along their length, but rather, the end loops are removed only by the axial motion of the filaments. Systems such as described above can position the distal end of a stent within ±5 mm of a desired axial location, according to use in an operation such as described in the following.

Use and Operation

Figure 2:
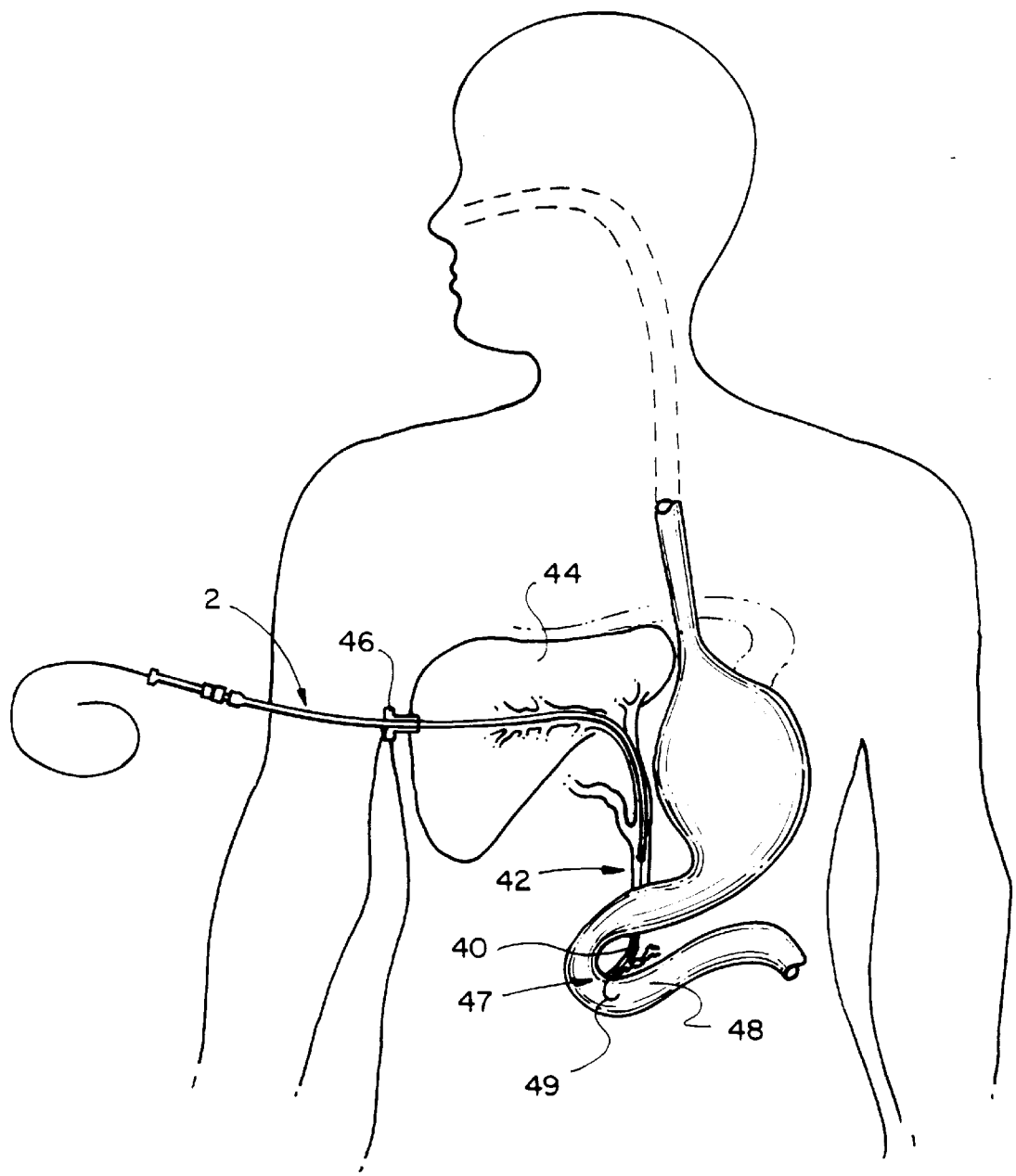
FIGS. 2–2f illustrate the operation and use of the system in FIG. 1.
Figure 2A:
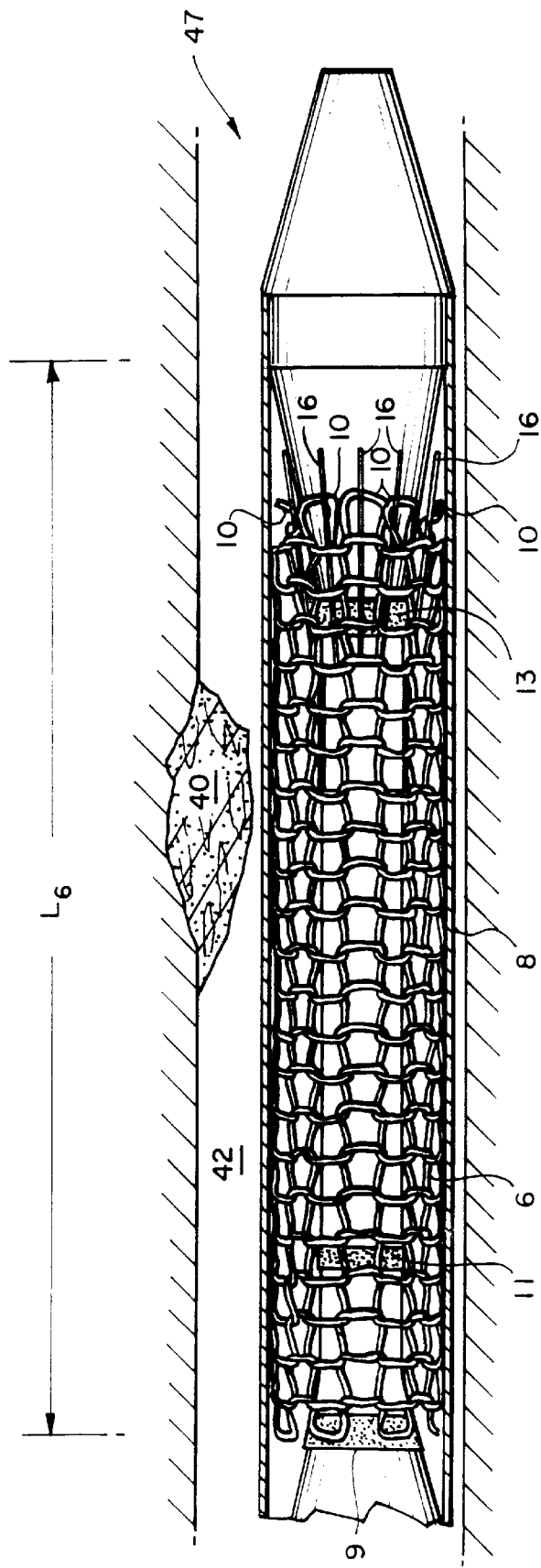
Figure 2B:
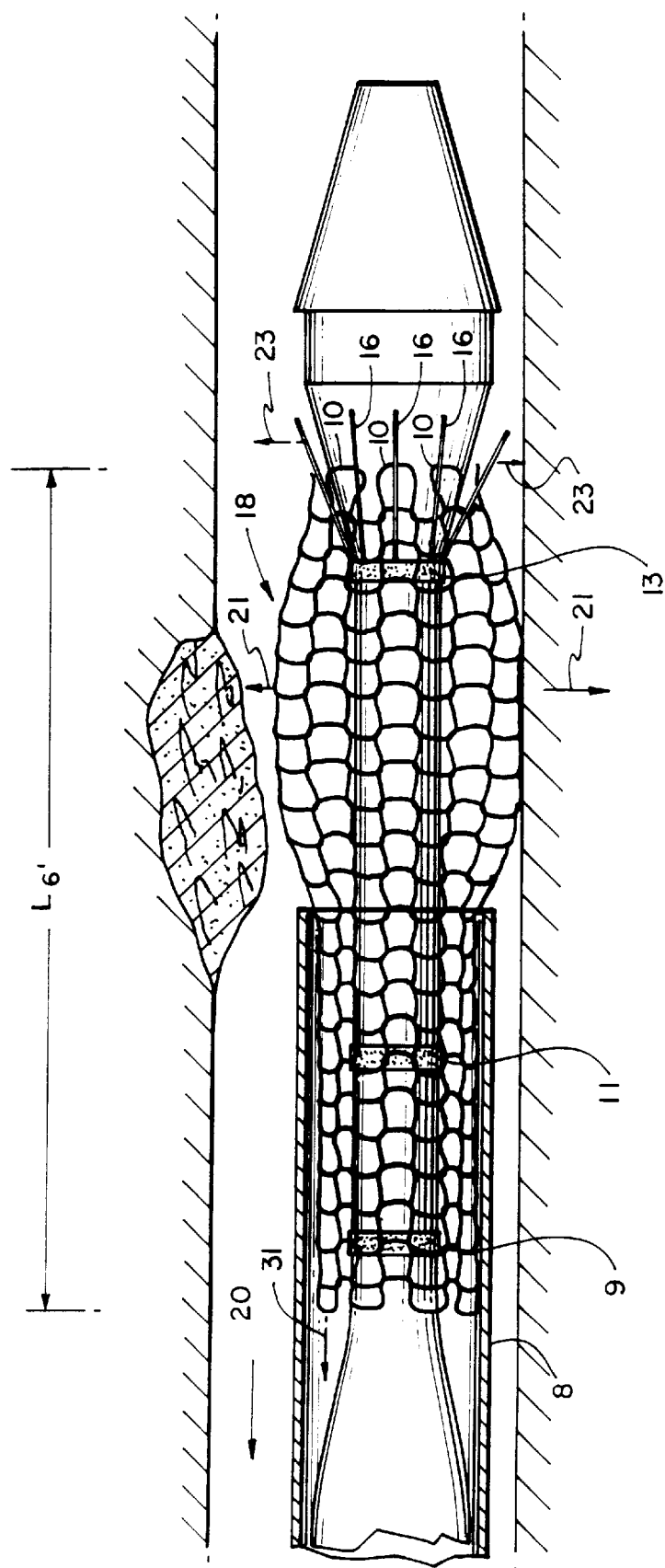
Figure 2D:
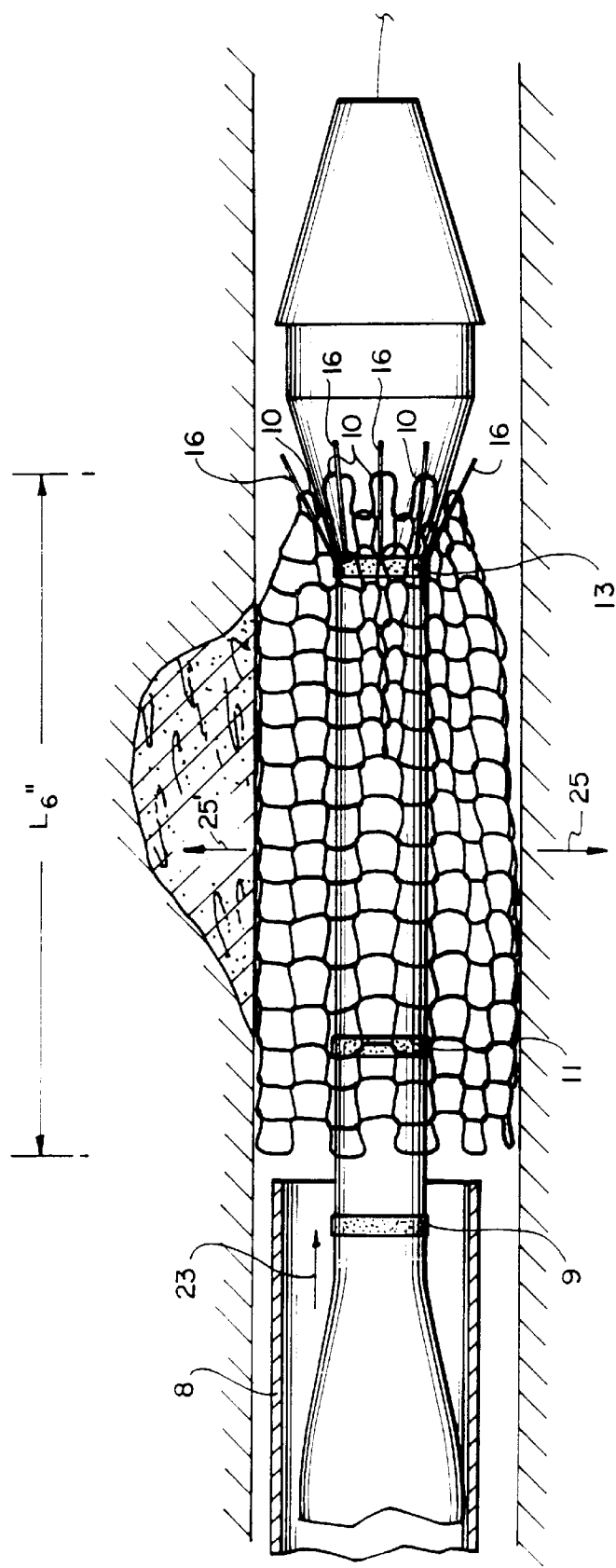
Figure 2F:
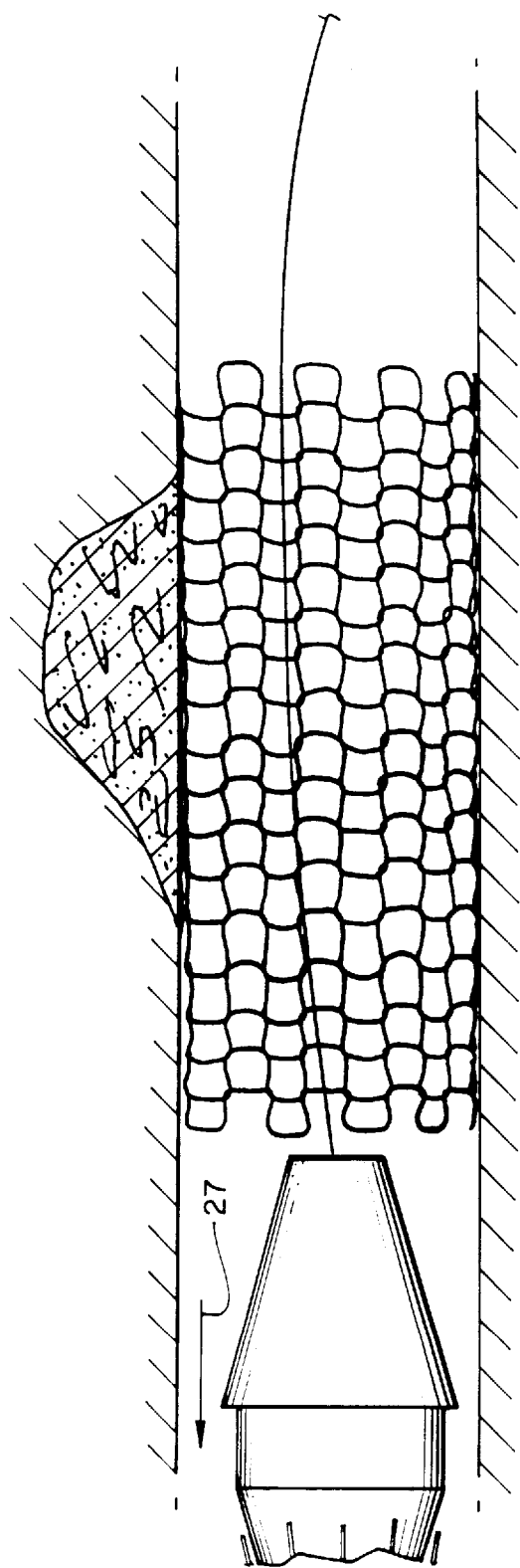

Referring now to FIGS. 2–2f, use of the delivery system for positioning a stent in the bile duct is illustrated. Referring to FIG. 2, the system may be used to treat an obstruction 40, such as a tumor, in the bile duct 42. The bile duct extends from the liver 44 to the duodenum 48. The system 2 is particularly useful for positioning a prosthesis in cases where the obstruction 40 is located near the duodenum 48. In such cases, it is particularly important to position the distal end of the prosthesis so that the overlap with the duodenum is minimized. Otherwise the action of the duodenum may draw the prosthesis axially out of the bile duct into the intestine.

Typically, the occlusion substantially closes off the bile duct which has a healthy lumen diameter of about 8–10 mm. The obstruction is typically around 4 cm in length. To prepare the duct for the prosthesis, the physician accesses the liver with an access sheath 46. A collangeogram is taken to locate the occlusion. Using ultrasound or fluoroscopy, a guidewire 49 (0.038 inch) is positioned through the access sheath, liver 44 and into the bile duct 42, such that it crosses the lesion 40 and extends into the duodenum 48. A series of dilators (not shown), for example, hard teflon, are tracked over the guidewire to widen the bile duct, tissue of a shoe leather-like texture, in preparation for the stent. The largest dilator approximates the full healthy lumen diameter. Alternatively, the largest dilator approximates the maximum outer diameter of the system with the prosthesis in the compact state. Balloon expansion devices can be used to the same effect before the system is positioned in the duct (or sometimes after the stent has been placed in the lumen). After preparing the lumen, the system 2 is tracked over the guidewire, through the sheath 46, liver 44, and into the bile duct 42.

Referring to FIG. 2a, the system is slid axially distally until distal radiopaque marker 13 is positioned axially at a location at least about 1 cm distal of the occlusion 40. This location substantially corresponds to the position the distal end of the stent, when expanded, will engage the lumen wall. The location is selected so the stent 6 is positioned beyond the occlusion 40 but not too close to the end 47 of the bile duct. The marker 11 indicates the position of the proximal end of the stent in the expanded position and is such that the proximal end of the prosthesis will engage healthy tissue over a length of at least 1 cm. Where possible the stent is centered, based on the fully expanded length indicated by markers 11, 13, about the obstruction. The marker 9 indicates the proximal end of the stent when the stent is in the fully compact form, which has an overall length, $L_6$, about 10 cm.

Referring to FIG. 2b, the sheath is retracted in one continuous motion. (After the retraction begins in this embodiment, the sheath cannot be extended distally without catching on the expanded portions of the stent and possibly pushing the stent distally off of the members 16.) With the sheath 8 partially withdrawn, (arrow 20), portions 18 of the prosthesis expand (arrow 21), although not to full expanded diameter. The end loops 10 of the prosthesis are maintained in the compact state and without axial movement, by the members 16 which deflect outward slightly (arrows 23) when the sheath is removed. With the distal end of the stent being held axially by members 16, the friction between the inner wall of the sheath 8 and the portions of the prosthesis covered by the sheath places the stent under tension, causing the prosthesis to be elastically lengthened slightly (arrow 31) to a length, $L_6'$, about 10.2–10.4 cm. The lengthening of the prosthesis has a simultaneous effect of reducing the radial force the stent exerts on the wall of the sheath and, therefore, the frictional force between the inner wall of the sheath and the stent, allowing a smoother retraction of the sheath with less axial force.

Referring to FIG. 2c, as the sheath retraction continues, proximally beyond about 60% of the distance between markers 9 and 13, the frictional force between the stent and the wall of the sheath is overcome by the elastic forces of the stent, removing the tension on the stent, and causing the distal end of the stent to relax distally (arrow 23). As illustrated, the relaxation of the largely independent knit rows proceeds from distal portions to proximal portions, with more distal portions expanding (arrows 25) to full diameter and engaging tissue. The most distal end, including the end loops, remains compact and axially stable.

Referring to FIG. 2d, after sheath retraction continues but usually to a point less than marker 9, the proximal end of the expanding (arrows 25) and contracting (arrow 23) prosthesis exits the sheath and engages the lumen wall, forcing open the lumen to its normal diameter and firmly anchoring the stent so that it resists axial motion. (In some cases, the stent opens the lumen over an extended period of time.) The end loops 10 remain compact and axially stable, owing to the strands 16, as the elastic forces relax during the expansion of the proximal portions. The stent in this condition has a shorter length, $L_6^{1''}$, about 6 cm.

Referring to FIG. 2e, the prosthesis is released from the catheter by drawing the catheter proximally (arrow 27), which causes the end loops to be positioned at more distal positions along the members 16, until the radial force of the prosthesis causes the members to deflect outwardly (arrows 29), releasing the end loops from the members on catheter body, so the end loops expand to full diameter. Since the stent has been substantially relaxed during expansion of proximal portions, the end loops engage the lumen wall at the desired axial location, without substantial elastic rebound axially. After the end loops are released from the members, the free ends of the members deflect back to their rest positions closer to the taper 34.

Referring to FIG. 2f, the catheter is then removed from the body, leaving the prosthesis properly positioned.

Other Embodiments

Many other embodiments are possible. Other types of stents, e.g., nonknitted stents, such as woven stents, can be used. The engagement of the distal end of the stent may be achieved by other arrangements, beside the openings in the stent wall and wires illustrated above. For example, the systems could include a separate member for holding the distal end of the stent axially and a separate member for holding the distal end of the stent radially compact. The separate members may be separately actuatable. While the systems discussed above provide particular advantages when positioning self-expanding stents in that sheath retraction is made easier, advantages, such as accurate placement, can be gained with other stents, such as non-self-expanding, plastically deformable type stents. The systems can be sized and configured for use in various body lumens, such as the biliary tree or blood vessels, or any other lumen where accurate location of a stent is desired, e.g., when the occlusion is adjacent a side branch.

Still other embodiments are in the following claims.

What is claimed is:

1. A system for positioning a self-expanding prosthesis in contact with tissue within a patient, comprising:

a self-expanding prosthesis having a proximal end and a distal end and a tissue-engaging body therebetween, a catheter having a portion supporting a prosthesis in a radially compact form, said portion of said catheter supporting said prosthesis including members positioned to engage the distal end of said prosthesis to maintain corresponding portions of the prosthesis compact at a fixed axial position with respect to the catheter while other portions of said prosthesis are radially expanded to engage tissue, said distal end of said prosthesis engaged by said members being releasable from said catheter at said fixed axial position by relative axial motion between said members and said prosthesis, so that said members disengage from said prosthesis, a retractable sheath positioned over and in contact with said prosthesis when said prosthesis is in the compact form, and a tensioning element applying an axial force to said prosthesis to reduce frictional force between said sheath and said prosthesis while retracting said sheath to expose said prosthesis.

2. A method of positioning a prosthesis in the body, comprising:

providing a system for positioning a prosthesis in contact with tissue on the wall of a lumen of a patient, comprising:

a tubular prosthesis having a proximal and distal end and a tissue-engaging body therebetween, said prosthesis having a radially compact form for delivery into the patient, and, being radially expandable along its body for engaging tissue, the length of said prosthesis varying in dependence on expansion of said body, and said prosthesis being formed of a patterned filament and including a series of openings through the tissue-engaging body of said prosthesis about the circumference of said prosthesis, near the distal end, and said system further including a catheter having a portion for supporting said prosthesis coaxially about said portion in said compact form for delivery into the patient and constructed for expanding said prosthesis into contact with tissue, said portion including a series of elongate members arranged about the circumference of said catheter, fixed to said catheter, and extending generally along the axis of the catheter to free ends positioned to pass through corresponding openings about the circumference of the tissue-engaging body of said prosthesis, said members maintaining corresponding portions of said prosthesis radially compact at a predetermined axial location, while proximal portions of said prosthesis are radially expanded to engage tissue, said portion of said prosthesis corresponding to said openings releasable from said catheter at an axial location substantially corresponding to said predetermined location by moving said catheter proximally so the free ends of said members are removed from said openings.

* * * * *